United States Patent
Hobel et al.

(10) Patent No.: US 10,259,841 B2
(45) Date of Patent: *Apr. 16, 2019

(54) METHOD FOR REDUCING THE DNA CONTENT OF A FERMENTATION BROTH

(71) Applicant: NOVOZYMES A/S, Bagsvaerd (DK)

(72) Inventors: Cedric Hobel, Kgs. Lyngby (DK); Heidi Winterberg Andersen, Vaerloese (DK); Peter Frode Pind, Herlev (DK); Cecilia Jansson Kepka, Bunkeflostrand (SE)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/306,941

(22) PCT Filed: Apr. 30, 2015

(86) PCT No.: PCT/EP2015/059497
§ 371 (c)(1),
(2) Date: Oct. 26, 2016

(87) PCT Pub. No.: WO2015/166037
PCT Pub. Date: Nov. 5, 2015

(65) Prior Publication Data
US 2017/0044209 A1 Feb. 16, 2017

(30) Foreign Application Priority Data

Apr. 30, 2014 (EP) .................................... 14166721

(51) Int. Cl.
*C12N 9/26* (2006.01)
*C12Q 1/68* (2018.01)
*C07K 1/14* (2006.01)
*C12N 9/82* (2006.01)
*C12N 15/10* (2006.01)

(52) U.S. Cl.
CPC ............... *C07K 1/14* (2013.01); *C07K 1/145* (2013.01); *C12N 9/2414* (2013.01); *C12N 9/82* (2013.01); *C12N 15/1003* (2013.01); *C12Y 302/01001* (2013.01); *C12Y 305/01001* (2013.01)

(58) Field of Classification Search
CPC .................................... C12N 9/26; C12Q 1/68
See application file for complete search history.

(56) References Cited

U.S. PATENT DOCUMENTS

2005/0037456 A1   2/2005   Lester
2014/0017735 A1*  1/2014   Brunecky ................ C12P 7/14
                                                            435/99

FOREIGN PATENT DOCUMENTS

| WO | 43502 | * | 7/2000 |
| WO | 2004/048588 A1 | | 6/2004 |
| WO | 2005/087791 A2 | | 9/2005 |
| WO | 2008/064686 A1 | | 6/2008 |

OTHER PUBLICATIONS

Anonymous, 2008, Review of coagulant market in CIS countries, Moskva, 11-14—English Translation.
Kurenkov, 1997, Soros educational journal, 57-63—English Translation.

* cited by examiner

*Primary Examiner* — Maryam Monshipouri
(74) *Attorney, Agent, or Firm* — Todd Sladek

(57) ABSTRACT

A method for reducing the level of DNA in a fermentation broth is disclosed where the method includes a heating step where the broth is heated to a temperature of at least 70° C.

21 Claims, 3 Drawing Sheets

METHOD FOR REDUCING THE DNA CONTENT OF A FERMENTATION BROTH

CROSS-REFERENCE TO RELATED APPLICATIONS

This application is a 35 U.S.C. 371 national application of PCT/EP2015/059497 filed Apr. 30, 2015, which claims priority or the benefit under 35 U.S.C. 119 of European application no. 14166721.2 filed Apr. 30, 2014, the contents of which are fully incorporated herein by reference.

FIELD OF THE INVENTION

The present invention relates to a method for obtaining a protein product from a fermentation broth wherein the fermentation broth has been subjected to a very effective process for removing host cell DNA.

BACKGROUND OF THE INVENTION

Production of protein products by fermentation is a well know process and it is used for production in industrial scale of many different proteins of interest. During fermentation some of the host cells producing the protein product of interest will break and the content of the cells, including DNA, will be released to the fermentation broth. Furthermore, in some fermentation the protein of interest is produced as an intracellular product. This means that the cells must lyse as a part of the purification process following the fermentation and this inevitably results in the release of significant amounts of DNA into the fermentation broth.

For some types of protein products it is desired to avoid residual DNA from the host cells producing the protein of interest, e.g. due to environmental or health concerns. Furthermore, DNA in the fermentation broth may increase the viscosity leading to a higher energy demand for stirring and or handling the fermentation broth.

There is therefore a need for method for removing or reducing the DNA content of fermentation broth.

However, it is very difficult to remove all residual host cell DNA from a fermentation broth, so there is a desideratum in the art to develop procedures to overcome the DNA problem.

SUMMARY OF THE INVENTION

It has surprisingly been found that subjecting a fermentation broth to heat is a very effective method to remove DNA so the present invention claims:
A method for removing DNA from a fermentation broth comprising a protein of interest and a microorganism producing the protein of interest, said method comprising:
  a) heating the fermentation broth to a temperature of at least 70° C.
The method preferably comprises the steps of:
  b) adding a poly aluminium chloride to the fermentation broth, and
  c) separating the flocculated microorganism from the fermentation broth.

The methods according to the invention will reduce the DNA level of the fermentation broth to a level below 1 μg/ml or even lower. In a preferred embodiment the DNA level is reduced to a level below the detection limit.

SHORT DESCRIPTION OF THE FIGURES

Figure 1:
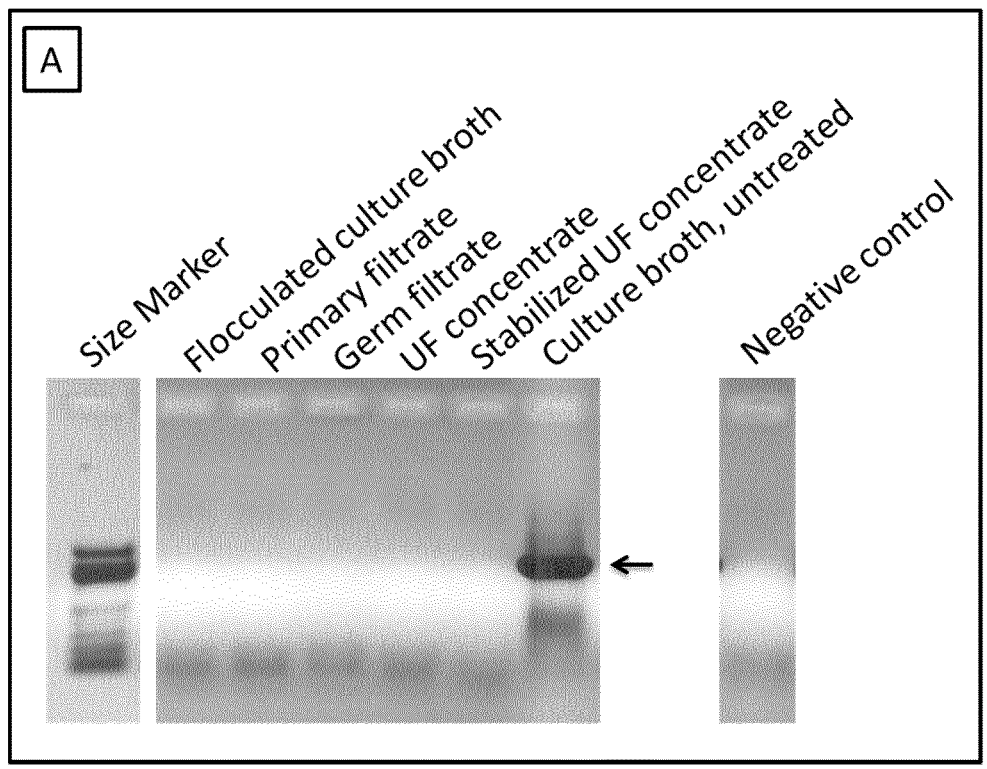

FIG. 1: Agarose gel electrophoresis of PCR-amplified genomic DNA of a *B. licheniformis* strain producing an amylase variant in pilot scale. The broth was submitted to heat treatment and flocculation prior to the enzyme recovery. Only the untreated broth has a positive DNA signal indicated by the band on the gel (arrow). The negative control supports that no false positive results are observed.

Figure 2:
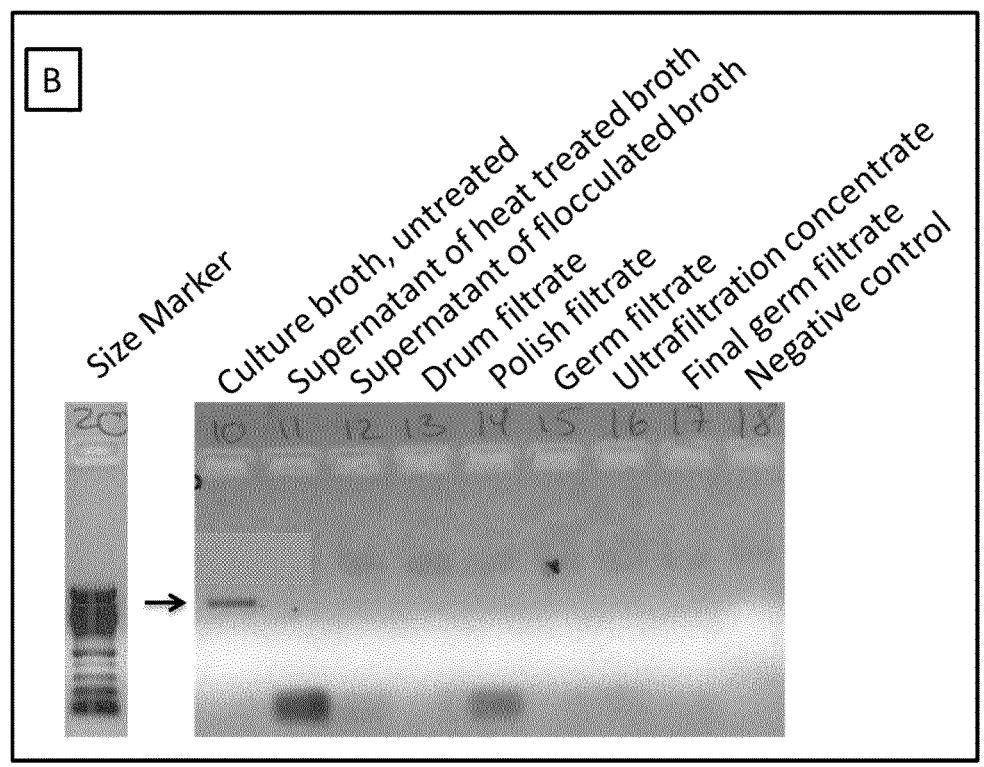

FIG. 2: Agarose gel electrophoresis of PCR-amplified genomic DNA of a *B. subtilis* strain producing an asparaginase in pilot scale. The broth was submitted to heat treatment and flocculation prior to the enzyme recovery. Only the untreated broth has a positive DNA signal indicated by the band on the gel (arrow). The negative control supports that no false positive results are observed.

Figure 3:
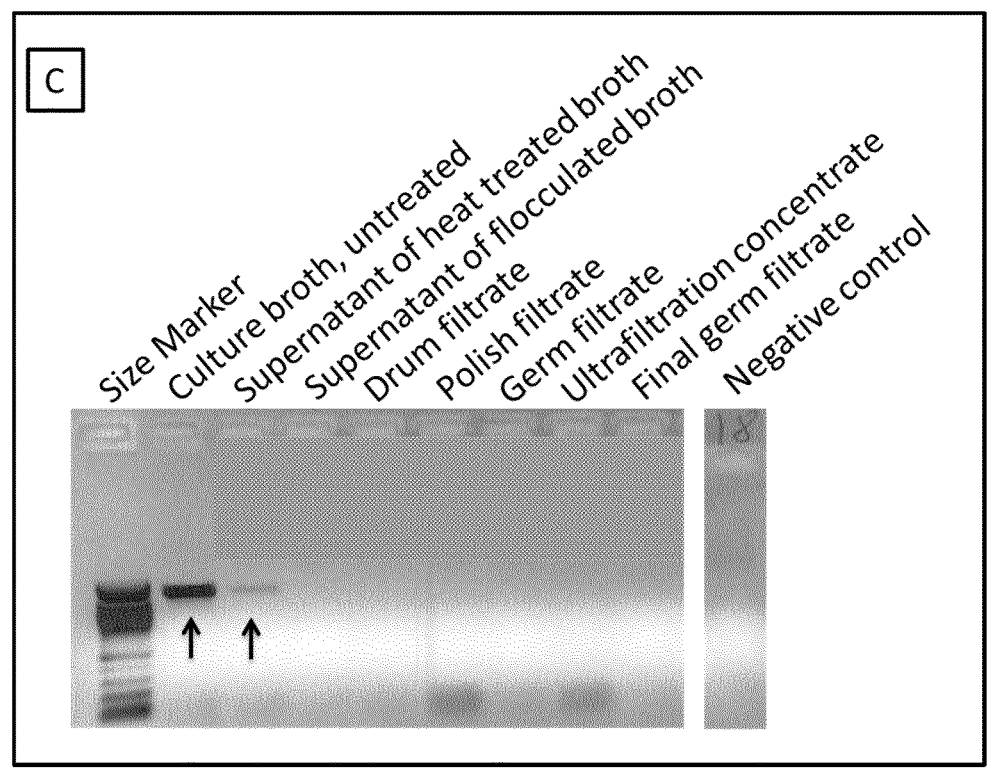

FIG. 3: Agarose gel electrophoresis of PCR-amplified genomic DNA of a *B. subtilis* strain producing an asparaginase in pilot scale. The broth was submitted to heat treatment and flocculation prior to the enzyme recovery. The untreated broth and the supernatant of the heat treated broth had a positive DNA signal indicated by a band on the gel (arrows); all other process streams have a negative signal. The negative control supports that no false positive results are observed.

DETAILED DESCRIPTION OF THE INVENTION

The present invention relates to a simple and very effective method for removing residual host cell DNA from a fermentation broth. Within the scope of this invention, host cell DNA is defined as including genomic DNA from the production strain and the fragment of DNA encoding for the protein of interest.

Microorganism Capable of Producing the Protein of Interest

The microbial host cell may be of any genus. The desired protein may be homologous or heterologous to the host cell capable of producing the protein of interest.

The term "homologous protein" means a protein encoded by a gene that is derived from the host cell in which it is produced.

The term "heterologous protein" means a protein encoded by a gene which is foreign to the host cell in which it is produced.

The term "recombinant host cell", as used herein, means a host cell which harbors gene(s) encoding the desired protein and is capable of expressing said gene(s) to produce the desired protein. The desired protein coding gene(s) may be transformed, transfected, transduced, or the like, into the recombinant host cell using techniques well known in the art.

When the desired protein is a heterologous protein, the recombinant host cell capable of producing the desired protein is preferably of fungal or bacterial origin. The choice of recombinant host cell will to a large extent depend upon the gene coding for the desired protein and the source of said protein.

The term "wild-type host cell", as used herein, refers to a host cell that natively harbors gene(s) coding for the desired protein and is capable of expressing said gene(s).

A "mutant thereof" may be a wild-type host cell in which one or more genes have been deleted, e.g., in order to enrich the desired protein preparation.

In a preferred embodiment, the recombinant or wild-type microbial host cell is a bacterium or a fungus.

The microbial host cell may be a yeast cell such as a *Candida*, *Hansenula*, *Kluyveromyces*, *Pichia*, *Saccharomyces*, *Schizosaccharomyces*, or *Yarrowia* strain. In another aspect, the strain is a *Saccharomyces carlsbergensis*, *Saccharomyces cerevisiae*, *Saccharomyces diastaticus*, *Saccha*-

*romyces douglasii, Saccharomyces kluyveri, Saccharomyces norbensis,* or *Saccharomyces oviformis* strain.

The microbial host cell may be a filamentous fungal strain such as an *Acremonium, Agaricus, Alternaria, Aspergillus, Aureobasidium, Bottyospaeria, Ceriporiopsis, Chaetomidium, Chrysosporium, Claviceps, Cochliobolus, Coprinopsis, Coptotermes, Cotynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* strain.

In another aspect, the strain is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium mops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* or *Trichoderma viride* strain.

In one aspect, the fungal host cell is a strain selected from the group consisting of *Candida, Hansenula, Kluyveromyces, Pichia, Saccharomyces, Schizosaccharomyces, Yarrowia, Acremonium, Aspergillus, Fusarium, Humicola, Mucor, Myceliophthora, Neurospora, Penicillium, Thielavia, Tolypocladium,* and *Trichoderma.*

In a more preferred embodiment, the filamentous fungal host cell is selected from the group consisting of *Trichoderma* and *Aspergillus* host cells, in particular a strain of *Trichoderma harzianum, Trichoderma koningii, Trichoderma longibrachiatum, Trichoderma reesei, Trichoderma viridel, Aspergillus awamori, Aspergillus fumigatus, Aspergillus foetidus, Aspergillus japonicus, Aspergillus nidulans, Aspergillus niger* or *Aspergillus oryzae,* especially a strain of *Trichoderma reesei.*

In another preferred embodiment, the recombinant or wild-type microbial host cell is a bacterium. Examples of microbial host cells include the ones selected from the group comprising gram positive bacteria such as a *Bacillus, Clostridium, Enterococcus, Geobacillus, Lactobacillus, Lactococcus, Oceanobacillus, Staphylococcus, Streptococcus,* or *Streptomyces,* or a Gram-negative bacteria such as a *Campylobacter, Escherichia, Flavobacterium, Fusobacterium, Helicobacter, Ilyobacter, Neisseria, Pseudomonas, Salmonella,* or *Ureaplasma.*

In one aspect, the bacterial host cell is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis.*

In another aspect, the bacterial host cell is a *Streptococcus equisimilis, Streptococcus pyogenes, Streptococcus uberis,* or *Streptococcus equi* subspecies *Zooepidemicus.*

In another aspect, the bacterial host cell is a *Streptomyces murinus, Streptomyces achromogenes, Streptomyces avermitilis, Streptomyces coelicolor, Streptomyces griseus,* or *Streptomyces lividans* strain. In another aspect, the bacterial host cell is *Escherichia coli.*

In another aspect, the bacterial host cell is selected from the group consisting of *Bacillus, Streptomyces, Escherichia, Buttiauxella* and *Pseudomonas.*

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

Protein of Interest

According to the present invention, the protein of interest may be a peptide or a polypeptide. A preferred peptide according to this invention contains from 5 to 100 amino acids; preferably from 10 to 80 amino acids; more preferably from 15 to 60 amino acids. A preferred peptide to be recovered according to the invention is an antimicrobial peptide, a lipopeptide or another functional peptide like brazzein.

A preferred polypeptide may be any protein that may be produced by a microorganism.

In a preferred embodiment, the protein of interest is an enzyme. In a preferred embodiment, the method is applied to a hydrolase (class EC 3 according to Enzyme Nomenclature; Recommendations of the Nomenclature Committee of the International Union of Biochemistry). Chemically modified or protein engineered mutants are included.

In a particularly preferred embodiment, an enzyme selected from the group consisting of an amylase, a protease, a lipase, a cellulase, a xylanase, a mannanase, a phytase, a xylose isomerase, a lactase, an acetolactate decarboxylase, a pectinase, a cutinase, a lyase, an arabinase, a galactanase, an oxidase, a laccase peroxidase and an asparaginase is preferred.

In another preferred embodiment the protein of interest is a protein having a high stability towards thermal inactivation, and which consequently is capable of being exposed to the heat treatment of the invention without unacceptable high losses of the functional protein. Thus in a particular preferred embodiment, the protein of interest is a thermostable enzyme. The thermostable enzyme may have a thermostability measured as a halflife at 70° C. and pH 7.0 is at least 30 minutes, preferably at least 40 minutes, preferably at least 50 minutes, preferably at least 60 minutes, preferably at least 70 minutes, preferably at least 80 minutes, preferably at least 90 minutes and most preferred at least 100 minutes. Examples of thermostable enzymes for which the method of the invention is suitable includes thermostable asparaginase disclosed in WO 2008/110513, WO 2014/027062 and WO2008/151807.

Amylases:

An amylase may be the desired enzyme produced according to the invention. Amylases include alpha-amylases, beta-amylases, pullulanases and maltogenic amylases.

An alpha-amylase may be derived from the genus *Bacillus*, such as, derived from a strain of *B. licheniformis, B. amyloliquefaciens, B. subtilis* and *B. stearothermophilus*. Other alpha-amylases include alpha-amylase derived from the strain *Bacillus* sp. NCIB 12289, NCIB 12512, NCIB 12513 or DSM 9375, all of which are described in detail in WO 95/26397, or the alpha-amylase described by Tsukamoto et al., Biochemical and Biophysical Research Communications, 151 (1988), pp. 25-31.

Other alpha-amylases include alpha-amylases derived from a filamentous fungus, preferably a strain of *Aspergillus*, such as, *Aspergillus oryzae* and *Aspergillus niger*.

In a preferred embodiment, the desired enzyme is an alpha-amylase derived from *Aspergillus oryzae* such as the one having the amino acid sequence shown in SEQ ID NO: 10 in WO 96/23874.

The desired enzyme may also be an alpha-amylase derived from *A. niger*, especially the one disclosed as "AMYA_ASPNG" in the Swiss-prot/TeEMBL database under the primary accession no. P56271.

The desired enzyme may also be a beta-amylase, such as any of plants and microorganism beta-amylases disclosed in W. M. Fogarty and C. T. Kelly, Progress in Industrial Microbiology, vol. 15, pp. 112-115, 1979.

The desired enzyme may also be a maltogenic amylase. A "maltogenic amylase" (glucan 1,4-alpha-maltohydrolase, E.C. 3.2.1.133) is able to hydrolyze amylose and amylopectin to maltose in the alpha-configuration. A maltogenic amylase of interest is the one derived from *Bacillus stearothermophilus* strain NCIB 11837. Maltogenic alpha-amylases are described in U.S. Pat. Nos. 4,598,048; 4,604,355; and 6,162,628.

Commercially available amylases are Duramyl™, Termamyl SC™, Termamyl Ultra™, Stainzyme™, Natalase™, Novamyl™ and BAN™ (Novozymes NS), Rapidase™ and Purastar™ (from DuPont).

The desired enzyme may also be a pullulanase including glucoamylase (EC 3.2.1.41), which acts on the non-reducing ends of pullulan to produce glucose also termed as a-dextrin 6-glucanohydrolase or true pullulanase or limit dextrinase, pullulanase which acts on a-(1,6)-glucosidic linkage in pullulan to produce maltotriose, isopullulanase, which hydrolyzes a-(1,4)-linkage to produce isopanose, and neopullulanase, which acts on a-(1,4)-linkage to produce panose.

Proteases:

Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Other suitable proteases are the *Nocardiopsis* proteases described in, e.g., WO 2005/115445 useful for pancreatic enzyme replacement.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase®, Opticlean®, Optimase®, and Excellenz P1000 (DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases or Cutinases:

A lipase is an enzyme that catalyzes the hydrolysis or formation of lipids. Lipases include enzymes defined by EC 3.1.1.3. Suitable lipases and cutinases include those of bacterial or fungal origin. Chemically modified or protein engineered mutant enzymes are included. Examples include lipase from *Thermomyces*, e.g., from *T. lanuginosus* (previously named *Humicola lanuginosa*) as described in EP258068 and EP305216, cutinase from *Humicola*, e.g., *H. insolens* (WO96/13580), lipase from strains of *Pseudomonas* (some of these now renamed to *Burkholderia*), e.g., *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), *Streptomyces griseus* (WO11/150157) and *S. pristinaespiralis* (WO12/137147), cutinase from *Magnaporthe grisea* (WO10/107560), cutinase from *Pseudomonas mendocina* (U.S. Pat. No. 5,389,536) and lipase from *Thermobifida fusca* (WO11/084412). Other useful lipases may be a *Bacillus* lipase, e.g., from *B. subtilis* (Dartois et al. (1993), Biochemica et Biophysica Acta, 1131, 253-360), *B. stearothermophilus* (JP 64/744992, WO11/084599), *Geobacillus stearothermophilus* lipase (WO11/084417), or *B. pumilus* (WO 91/16422.

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes NS), Lumafast (originally from Genencor) and Lipomax (originally from Gist-Brocades).

Still other examples are lipases sometimes referred to as acyltransferases or perhydrolases, e.g., acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase.

Other suitable lipases are the lipases described in, e.g., WO 2006/136159 useful for pancreatic enzyme replacement.

Cellulases:

Cellulases include enzymes that act on cellulose directly and accessory enzymes that facilitate the direct action of other enzymes on cellulose. Suitable cellulases include those of bacterial or fungal origin such as exoglucanases or exocellobiohydrolases, and/orendoglucanases and/or beta-glucosidases. These different types of cellulose enzymes act synergistically to convert cellulose and its derivatives to glucose. Cellulase enzymes also include accessory enzymes, including GH61 members, such as EG4, swollenin, Loosenin, CIP1 and the like. Suitable cellulases include cellulases from the genera *Bacillus, Pseudomonas, Humicola,*

*Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme™, Carezyme™, and Celluclean™ (Novozymes NS), Clazinase™, and Puradax™ HA (DuPont), and KAC-500(B)™ (Kao Corporation).

Xylanases:

Xylanases include 1,4-(beta)-D-xylan-xylanohydrolase, (EC 3.2.1.8), 4-xylanohydrolase, endo-1,4-xylanase, endo-1,4-beta-xylanase, beta-1,4-xylanase, endo-1,4-beta-D-xylanase, 1,4-beta-xylan xylanohydrolase, beta-xylanase, beta-1,4-xylan xylanohydrolase, beta-D-xylanase which degrade the linear polysaccharide beta-1,4-xylan into xylose, thus breaking down hemicellulose, one of the major components of plant cell walls. An example of a commercially available xylanase is Econase™ (AB Vista).

Asparaginases:

Asparaginase also called L-asparaginase and L-asparagine amidohydrolase. (EC 3.5.1.1) is an enzyme that catalyzes the hydrolysis of asparagine to aspartic acid.

Acrylaway™ (Novozyme A/S) is a example of a commercially available asparaginase.

Mannanases:

Mannanases (EC 3.2.1.25) include all enzymes catalyzing the hydrolysis of terminal, non-reducing beta-D-mannose in beta-D-mannosides, also called mannanes.

A commercial example of mannanases is Mannaway™ (Novozymes A/S).

Phytases:

In the present context a phytase is an enzyme which catalyzes the hydrolysis of phytate (myo-inositol hexakisphosphate) to (1) myo-inositol and/or (2) mono-, di-, tri-, tetra- and/or penta-phosphates thereof and (3) inorganic phosphate.

Phytases include 3-phytase (myo-inositol hexaphosphate 3-phosphohydrolase, EC 3.1.3.8) and 6-phytase (myo-inositol hexaphosphate 6-phosphohydrolase, EC 3.1.3.26).

Examples of commercially available phytases include Ronozyme™ (DSM Nutritional Products), Natuphos™ (BASF), Finase™ (AB Vista), Quantum™ XT and Blue (AB Vista), the Phyzyme™ product series (DuPont) and the Axtra™ PHY product series (DuPont). Other preferred phytases include those described in WO 98/28408, WO 00/43503, and WO 03/066847.

Lyases:

The lyase may be a pectate lyase of bacterial or fungal origin. Chemically or genetically modified mutants are included. In a preferred embodiment the pectate lyase is derived from *Bacillus*, particularly *Bacillus substilis, B. licherniformis* or *B. agaradhaerens*, or a variant derived of any of these, e.g. as described in U.S. Pat. No. 6,124,127, WO 1999/027083, WO 1999/027084, WO 2002/006442, WO 2002/092741, WO 2003/095638, Commercially available pectate lyases include XPect; Pectawash™ and Pectaway™ (Novozymes A/S).

Acetolatate decarboxylase (EC 4.1.1.5) belongs to the group of enzymes called lyases, specifically the carboxylyases, which cleave carbon-carbon bonds. The commercial enzyme Maturex™ (Novozymes A/S) is used widely in the brewing industry.

Xylose Isomerases:

A commercially available xylose isomerase is for example Sweetzyme™ (Novozymes A/S) or GenSweet™ (DuPont).

Lactases:

Lactose, a dimer of glucose and galactose is the predominant sugar in milk that is responsible to a large extent to milk intolerance in mammals, especially humans. Beta-galactosidases or Lactases (EC 3.2.1.23) hydrolyse the dimer in the individual carbohydrates thereby increasing the tolerance and ability to digest milk during consumption. Alternative names to lactase include also exo-(1,4)-beta-D-galactanases.

Commercially available lactases include for instance Lactozyme Pure™ (Novozymes A/S) and GODO-YNL2 lactase (DuPont).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Other peroxidases include Guardzyme™ (Novozymes A/S).

In a particular embodiment the present invention does not cover enzymes which are destroyed by heat. In a more particular embodiment the invention does not comprise enzymes which are destroyed by a temperature above 65° C., 70° C., 80° C., 90° C. and/or 100° C.

Fermentation Broth

The present invention may be useful for any fermentation in industrial scale, e.g., for any fermentation having culture media of at least 50 liters, preferably at least 500 liters, more preferably at least 5,000 liters, even more preferably at least 50,000 liters.

The microorganism producing the protein of interest may be fermented by any method known in the art. The fermentation medium may be a minimal medium as described in, e.g., WO 98/37179, or the fermentation medium may be a complex medium comprising complex nitrogen and carbon sources, wherein the complex nitrogen source may be partially hydrolyzed as described in WO 2004/003216.

The fermentation may be performed as a batch, a repeated batch, a fed-batch, a repeated fed-batch or a continuous fermentation process.

In a fed-batch process, either none or part of the compounds comprising one or more nutrient(s) is added to the medium before the start of the fermentation and either all or the remaining part, respectively, of the compounds comprising one or more nutrients are fed during the fermentation process. The compounds which are selected for feeding can be fed together or separately to the fermentation process.

In a repeated fed-batch or a continuous fermentation process, the complete start medium is additionally fed during fermentation. The start medium can be fed together with or separately from the structural element feed(s). In a repeated fed-batch process, part of the fermentation broth comprising the biomass is removed at regular time intervals, whereas in a continuous process, the removal of part of the fermentation broth occurs continuously. The fermentation process is thereby replenished with a portion of fresh medium corresponding to the amount of withdrawn fermentation broth.

In a preferred embodiment of the invention, a fermentation broth from a fed-batch fermentation process is preferred.

Temperature

It has surprisingly been found that heating the fermentation broth to above 65° C. such as above 70° C. is an efficient method for reducing the DNA in a fermentation broth.

The fermentation broth may be heated to a temperature of at least or above 65° C., 70° C., 75° C., 80° C. or even above 85°.

In order not to denature the protein of interest such as an enzyme, it is important to keep the temperature of the fermentation broth below the denaturing temperature of the protein.

The temperature may be kept below 110° C., 100° C., 95° C. or even below 90° C.

The temperature may be increased to between 65° C. to 110° C., 65° C. to 100° C., 70° C. to 110° C., 70° C. to 100° C., 75° C. to 110° C., 75° C. to 100° C., 75° C. to 95° C. or 80° C. to 90° C.

In a preferred embodiment the heating of the fermentation broth result in no loss or insignificant loss of protein stability or activity, e.g. less than 1%, 2%, 5%, 10%, 15%, 20% or 25% loss of activity of desired protein. Loss of protein stability or activity may be determined by measuring the amount of the protein of interest present in the fermentation broth immediately before and immediately after the heat treatment.

In this connection loss of protein or activity is typically measured using a standard assay for the protein of interest and is not limited to a particular type of assay. As examples of suitable assays for use in the invention can be mentioned assays for enzymatic activity, ELISA methods and immunological assays. If the protein of interest is an enzyme the assay for measuring loss of activity is preferably an assay measuring the enzymatic activity of the enzyme.

Time

The fermentation broth may be heated for at least 5, 10, 20, 30, 40, 60, 90, 120, 150, 180 or even up to 240 min or up to 6 hours.

In a preferred embodiment the fermentation broth is heated less than 240, 200, 180, 150, 120 or even less than 90 min.

In a particular embodiment the fermentation broth may be heated between 20 and 120 min, such as between 30 and 90 min.

Equipment for Heating

Any suitable equipment may be used for heating the fermentation broth and the following shall not be seen as limiting.

The temperature in the fermentation broth may be increased by steam injection or use of heating jackets. Other possible heating solutions include passive heating (microbial heat), heat exchanger with subsequent hold in a vessel or pipe loop, external loops and flow through cells.

The method of the invention may be applied to an untreated fermentation broth or to a fermentation broth that has first been subjected to, but not limited to, e.g., a pH adjustment.

Dilution

According to the present invention, the fermentation broth may be diluted up to 2000% (w/w) with water; preferably the fermentation broth may be diluted 10-2000% (w/w) with water; more preferably the fermentation broth may be diluted 100-1500% (w/w) with water; more preferably the fermentation broth may be diluted 100-1000% (w/w) with water; more preferably the fermentation broth may be diluted 200-800% (w/w) with water.

Dilution with water means, according to the present invention, that the dilution medium may be water, or it may be an ultra filtration permeate from the production of the protein of interest, or it may be a recycle of water from the production of the protein of interest, or it may be a condensate from a heater, or it may be any combination of the above mentioned, e.g., a mixture of water and an ultra filtration permeate.

Flocculation

In order to flocculate the fermentation broth a divalent salt may be added to the fermentation broth, in particular a calcium salt and/or a magnesium salt, e.g., calcium chloride or magnesium chloride. A preferred embodiment is a calcium salt, in particular calcium chloride.

The salt may be added to the fermentation broth in a concentration of 0.01-10% (w/w) per kg fermentation broth (un-diluted); preferably 0.5-10% (w/w) per kg fermentation broth (un-diluted); more preferably 1-9% (w/w) per kg fermentation broth (un-diluted); in particular 2-8% (w/w) per kg fermentation broth (un-diluted).

Poly Aluminum Compound

To further improve removal of the DNA from the fermentation broth a poly aluminium compound may be added to the fermentation broth. Many Aluminium compounds are known to improve flocculation, e.g., $Al_2(SO_4)_3$, $NaAlO_2$, $K_2Al_2O_4$, $AlCl_3$, $Al(NO_3)_3$, Al-acetate, and Al-formate.

Particular useful poly aluminium chlorides include compounds of the formula $Al_n(OH)_mCl_{(3n-m)}$ and poly aluminium chlorides and aluminium chlorohydrates with the CAS No.: 1327-41-9.

Examples of useful poly aluminium chlorides comprise aluminum chlorohydrate, GC850™ ($Al_2(OH)_5Cl$) obtainable from Gulbrandsen or NordPac 18 (available from Nordisk Aluminat A/S, Denmark) which is an aluminium complex with the brutto formula $Al(OH)_{1,2}Cl_{1,8}$. Another example of a useful poly aluminium chloride with the formula $Al(OH)_{1,2}Cl_{1,8}$ is PAX-XL 100 (available from Kemira). Another two examples of useful poly aluminium chloride are PAC (available from Shanghai Haotian Water Treatment Equipment Co., Ltd supplied in solid form) or PAC (available from Tianjin Kairuite technology Ltd. Supplied in liquid form). Another example of useful poly aluminium chloride with the formula $Al(OH)_{1,2}Cl_{1,8}$ is PAX18 (available from Kemira Water Solutions).

The concentration of the poly aluminium chloride will normally be in the range of 0.1-10%) (w/w) calculated per kg fermentation broth (un-diluted); preferably in the range of 0.5-5%) (w/w) calculated per kg fermentation broth (un-diluted).

After addition of the poly aluminium chloride, the pH may be adjusted. The pH may be adjusted to a pH within a range of pH 2 to pH 11. The pH may be adjusted with any acid or base as known in the art.

The poly aluminium chloride may also be added after the microorganism has been separated from the fermentation broth.

The poly aluminium chloride may also be added in two or more steps: e.g., before the microorganism is removed from the fermentation broth; and then again after the microorganism has been removed such as in the subsequent downstream process liquid.

Polymers

Polymers are widely used for particle aggregation. Anionic and cationic polymers are preferred. A useful cationic polymer may be a polyamine, and a useful anionic polymer may be a polyacrylamid. Useful polymer concentrations will normally be in the range of 0.5-20% (w/w) calculated per kg fermentation broth (un-diluted); preferably in the range of 1-10% (w/w) calculated per kg fermentation broth (un-diluted).

An example of a useful anionic polymer is SuperflocT™ A 130 (Kemira). Examples of useful cationic polymers are Polycat™ (Kemira), C521 (Kemira), and C591 (Kemira).

Subsequent Downstream Operations

The flocculated cells may be removed by methods known in the art such as, but not limited to, filtration, e.g., drum filtration, membrane filtration, filter-press dead end filtration, cross-flow filtration, or centrifugation.

The resulting protein solution may then be further processed or refined by methods known in the art. For example, the protein may be recovered by conventional procedures including, but not limited to, further filtration such as ultra-filtration and dia-filtration, extraction, spray-drying, evaporation, precipitation or crystallization. The isolated protein may then be further purified and/or modified by a variety of procedures known in the art including, but not limited to, chromatography e.g. ion exchange, affinity, hydrophobic, chromatofocusing, and size exclusion and/or electrophoretic procedures e.g. preparative isoelectric focusing and/or differential solubility e.g., ammonium sulfate precipitation and/or extraction.

Detection of Residual Host Cell DNA

The term residual host cell DNA is including genomic DNA from the production strain and the fragment of DNA encoding for the protein of interest.

The detection and quantification of minute amounts of residual host cell DNA may be accomplished by various methods known in the art. Many methods are developed to measure specific single target sequences. Examples of methods are:

- A hybridization-based method for the detection of the specific DNA of defined origin with dot blots and hybridization of radioisotope-labeled DNA probes using random hexamers to generate representative probes covering the whole genome of the host cells.
- A quantitative PCR-based method for the detection of specific DNA of defined origin targeting a specific gene sequence for amplification and calibration using purified, species-matched, genomic DNA.
- A qualitative PCR method for the detection of specific DNA of defined origin targeting a specific gene sequence for amplification and calibration using purified, species-matched, genomic DNA. A threshold is determined based on the lowest amount of genome DNA that can be detected using the method.

According to the present invention purification of trace DNA was accomplished by use of the FastDNA™ Spin Kit (MP Biomedicals). The eluted sample was then subjected to a PCR reaction using specific primers for a chromosomal locus on the host cell. Positive controls are included where known amounts of host DNA is added to PCR reactions in different concentrations. After the PCR reaction the samples are subjected to gel-electrophoresis and intensity of the DNA bands compared to estimate the concentration of the host DNA in the original sample. Detailed protocols for PCR are provided in Innis et aL (1990) PCR Protocols, A Guide to methods and applications, Academic Press inc., N.Y.

Treatment of a fermentation broth or other protein preparation using the present method results in significant reduction in amounts of DNA being present in the fermentation broth, and preferably the DNA content is reduced to an undetectable level. A level is considered undetectable if PCR amplification of any segment of genomic DNA present in a single copy in a haploid genome followed by ethidium bromide staining gives no visible band.

Preferably the DNA level in the fermentation broth is reduced to a level below 1 µg/ml, preferably below 500 ng/ml, preferably below 200 ng/ml, preferably below 100 ng/ml, preferably below 50 ng/ml, preferably below 20 ng/ml, preferably below 10 ng/ml, preferably below 5 ng/ml, preferably below 2 ng/ml preferably below 1 ng/ml, and most preferred below 500 pg/ml.

In an example of a typical regulatory environment, no detectable DNA, may be ascertained using a PCR-based assay with a detection limit of, for example 1, 5, 10 or 20 ng/mL enzyme preparation.

In addition, the use of the instant method in combination with conventional methods of removing DNA from fermentation broths or other protein preparation is also contemplated.

The invention is further summarized in the following paragraphs:

1. A method for removing DNA from a fermentation broth comprising a protein of interest and a microorganism producing the protein of interest, said method comprising:
    a) heating the fermentation broth to a temperature of at least 70° C.
2. The method according to paragraph 1, further comprising the steps of:
    b) adding a poly aluminium chloride to the fermentation broth, and
    c) separating the flocculated microorganism from the fermentation broth.
3. The method according to paragraph 1 or 2, wherein the protein of interest is a peptide or a polypeptide.
4. The method according to paragraph 3, wherein the protein of interest is a peptide containing from 5 to 100 amino acids.
5. The method according to paragraph 4, wherein the protein of interest is a peptide containing from 10 to 80 amino acids.
6. The method according to paragraph 5, wherein the protein of interest is a peptide containing from 15 to 60 amino acids.
7. The method according to paragraph 3, wherein the protein of interest is an antimicrobial peptide, a lipopeptide or brazzein.
8. The method according to paragraph 3, wherein the protein of interest is an enzyme.
9. The method of paragraph 8, wherein the enzyme is selected among: hydrolases, lyases, proteases, amylases glucoamylases, pectinases, pectate lyases, cellulases, xylanases, arabinases, arbinofuranosidases, mannanases, carrageenanases, xanthanases, endoglucanases, chitinases, asparaginases, lipases, phospholipases, cutinases, lysozymes, phytases, peroxidases, lactase, glucose isomerases, xylose isomerases, esterases and phosphodiesterases.
10. The method according to paragraph 8 or 9, wherein the enzyme is a thermostable enzyme.
11. The method according to paragraph 10, wherein the thermostable enzyme has a thermostability measured as halflife at 70° C. and pH 7.0 of at least 30 minutes.
12. The method according to paragraph 11, wherein the thermostable enzyme has a thermostability measured as halflife at 70° C. and pH 7.0 of at least 40 minutes.
13. The method according to paragraph 12, wherein the thermostable enzyme has a thermostability measured as halflife at 70° C. and pH 7.0 of at least 50 minutes.

14. The method according to paragraph 13, wherein the thermostable enzyme has a thermostability measured as halflife at 70° C. and pH 7.0 of at least 60 minutes.
15. The method according to paragraph 14, wherein the thermostable enzyme has a thermostability measured as halflife at 70° C. and pH 7.0 of at least 70 minutes.
16. The method according to paragraph 15, wherein the thermostable enzyme has a thermostability measured as halflife at 70° C. and pH 7.0 of at least 80 minutes.
17. The method according to paragraph 16, wherein the thermostable enzyme has a thermostability measured as halflife at 70° C. and pH 7.0 of at least 90 minutes.
18. The method according to paragraph 17, wherein the thermostable enzyme has a thermostability measured as halflife at 70° C. and pH 7.0 of at least 100 minutes.
19. The method according to any of paragraphs 10 to 18, wherein the thermostable enzyme is an amylase or an asparaginase.
20. The method according to any of the preceding paragraphs, wherein the microorganism is a bacterium or a fungus.
21. The method according to paragraph 20, wherein the microorganism is a fungus selected from the group consisting of *Trichoderma* and *Aspergillus* host cells.
22. The method according to paragraph 21 wherein the fungus is a strain of *Trichoderma harzianum, Trichoderma koningii, Trichoderma longibrachiaturn, Trichoderma reesei, Trichoderma viridel, Aspergillus awamori, Aspergillus fumigatus, Aspergillus foetidus, Aspergillus japonicus, Aspergillus nidulans, Aspergillus niger* or *Aspergillus oryzae.*
23. The method according to paragraph 20, wherein the microorganism is a bacterium from the group comprising gram positive bacteria such as a *Bacillus, Clostridium, Enterococcus, Geobacillus, Lactobacillus, Lactococcus, Oceanobacillus, Staphylococcus, Streptococcus,* or *Streptomyces,* or a Gram-negative bacteria such as a *Campylobacter, Escherichia, Flavobacterium, Fusobacterium, Helicobacter, Ilyobacter, Neisseria, Pseudomonas, Salmonella,* or *Ureaplasma.*
24. The method according to paragraph 23, wherein the bacterial host cell is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis.*
25. The method according to any of the preceding paragraphs, wherein the temperature of the fermentation broth is heated to at least 75° C.
26. The method according to paragraph 25, wherein the temperature of the fermentation broth is heated to at least 80° C.
27. The method according to any of paragraph 1 to 24, wherein the temperature of the fermentation broth is heated to a temperature between 70° C. and 110° C.
28. The method according to paragraph 27, wherein the temperature of the fermentation broth is heated to a temperature between 70° C. and 100° C.
29. The method according to paragraph 28, wherein the temperature of the fermentation broth is heated to a temperature between 70° C. and 90° C.
30. The method according to paragraph 27, wherein the temperature of the fermentation broth is heated to a temperature between 75° C. and 110° C.
31. The method according to paragraph 30, wherein the temperature of the fermentation broth is heated to a temperature between 75° C. and 100° C.
32. The method according to paragraph 31, wherein the temperature of the fermentation broth is heated to a temperature between 75° C. and 90° C.
33. The method according to any of the preceding paragraphs, wherein the temperature is kept at a temperature above 70° C. for a period between 2 min and 150 min.
34. The method according to paragraph 33, wherein the temperature is kept at a temperature above 70° C. for a period between 5 and 135 min.
35. The method according to paragraph 34, wherein the temperature is kept at a temperature above 70° C. for a period between 10 and 120 min.
36. The method according to paragraph 35, wherein the temperature is kept at a temperature above 70° C. for a period between 20 and 100 min.
37. The method according to any of the paragraphs 1 to 32, wherein the temperature is kept at a temperature above 70° C. for a period of for at least 10 min.
38. The method according to paragraph 37, wherein the temperature is kept at a temperature above 70° C. for a period of at least 20 min.
39. The method according to paragraph 38, wherein the temperature is kept at a temperature above 70° C. for a period of at least 30 min.
40. The method according to paragraph 39, wherein the temperature is kept at a temperature above 70° C. for a period of at least 40 min.
41. The method according to paragraph 40, wherein the temperature is kept at a temperature above 70° C. for a period of at least 50 min.
42. The method according to paragraph 41, wherein the temperature is kept at a temperature above 70° C. for a period of at least 60 min.
43. The method according to paragraph 42, wherein the temperature is kept at a temperature above 70° C. for a period of at least 70 min.
44. The method according to paragraph 43, wherein the temperature is kept at a temperature above 70° C. for a period of at least 80 min.
45. The method according to any of the preceding paragraphs, wherein the poly aluminium chloride is added in an amount of 0.1-10% (w/w) calculated per kg fermentation broth.
46. The method according to any of the preceding paragraphs, wherein one or more flocculating agents are added in addition to the poly aluminium chloride.
47. The method according to paragraph 46, wherein the flocculating agents are selected from the group consisting of salts and polymers.
48. The method according to paragraph 47, wherein the polymer is an anionic or a cationic polymer.
49. The method according to any of the preceding paragraphs, wherein the separation in step c) is performed by centrifugation or filtration.
50. The method according to paragraph 2, wherein pH is adjusted to a pH within the range of pH 2 to pH 11 after addition of the poly aluminium chloride.
51. The method according to any of the preceding paragraphs wherein the DNA level is reduced to a level below 1 μg/ml.
52. The method according to paragraph 51, wherein the DNA level is reduced to a level below 500 ng/ml.
53. The method according to paragraph 52, wherein the DNA level is reduced to a level below 200 ng/ml.

54. The method according to paragraph 53, wherein the DNA level is reduced to a level below 100 ng/ml
55. The method according to paragraph 54, wherein the DNA level is reduced to a level below 50 ng/ml.
56. The method according to paragraph 55, wherein the DNA level is reduced to a level below 20 ng/ml.
57. The method according to paragraph 56, wherein the DNA level is reduced to a level below 10 ng/ml.
58. The method according to paragraph 57, wherein the DNA level is reduced to a level below 5 ng/ml.
59. The method according to paragraph 58, wherein the DNA level is reduced to a level below 2 ng/ml.
60. The method according to paragraph 59, wherein the DNA level is reduced to a level below 1 ng/ml.
61. The method according to paragraph 60, wherein the DNA level is reduced to a level below 500 pg/ml.
62. The method according to paragraph 61, wherein the DNA is below detection limit.
63. The method according to paragraph 62 where the detection limit is determined by a PCR amplification of any segment of genomic DNA present in a single copy in a haploid genome followed by gel-electrophoresis and ethidium bromide staining, where the staining does not disclose any visible bands.
64. The method according to any of the preceding paragraphs, wherein there is less than 10 ng host cell DNA per gram fermentation broth after step b).
65. The method according to any of the preceding paragraphs, wherein the fermentation broth may be diluted up to 2000% (w/w) with water.

The invention is further illustrated in the following examples which are not intended to be in any way limiting to the scope of the invention as claimed.

EXAMPLES

Materials and Methods

Example 1

DNA Removal from a Fermentation Broth of an Amylase Variant by the Combination of Heat Treatment and Flocculation in Pilot Scale A submerged fermentation of a *Bacillus licheniformis* strain expressing an alpha-amylase variant was performed as known in the art.

The fermentation broth contained the protein of interest and the resulting broth had a demonstrated DNA content.

At the end of the standard fermentation the temperature of the broth was raised by means of controlled steam injection in the tank. The temperature was raised to reach 80° C. and the broth was maintained at this temperature for approximately 30 min. Once the heat treatment was executed, the fermentation broth was transferred in another tank with mixing and cooling/heating capacity by means of jackets surrounding the tank; the broth was cooled to reach 35° C. and was maintained at that temperature with constant mixing before being processed furthermore.

The fermentation broth was flocculated batch-wise according to the following instructions:

| Component | Amount | Concentration | Supplier |
|---|---|---|---|
| Heat-treated fermentation broth | 20 kg | — | |
| Tap water | 100.7 kg | — | |
| CaCl$_2$ | 0.46 kg | 100% | Tetra, Helsingborg, Sweden |
| GC850 ™ | 0.41 kg | 100% | Kemira Water, Copenhagen, Denmark |
| Superfloc C591 ™ | 5.44 kg | 10% | Kemira Water, Copenhagen, Denmark |
| Superfloc A130 ™ | 2.3 kg | 0.01% | Kemira Water, Copenhagen, Denmark |

The broth was diluted with warm tap water in order to keep a temperature of 35° C. through the first part of the enzyme recovery. pH was adjusted with acetic acid and/or sodium hydroxide solutions after the addition of the poly-aluminum salt GC850™ in order to reach the desired pH 10.5 set point.

The flocculated material was then submitted to a recovery process similar to the one used for standard production but down-scaled to pilot scale. All equipment units were operated according to the respective manufacturer's instructions and/or according to protocols as known in the art. The process included:
  Primary filtration on disposable HS2000 filter plates (Pall, Lund, Sweden),
  Germ filtration on disposable EKS filter modules (Pall, Lund, Sweden),
  Ultrafiltration (UF) on a semi-permeable UFX10 membrane (Alfa Laval, Lund, Sweden). The enzyme concentration obtained by ultrafiltration was equal to one observed in standard production.
  Stabilization of the UF concentrate with sucrose, pH control and adjustment. The amount of sucrose used for stabilization was identical to the one used in standard production.

Samples were taken at all streams mentioned here above and submitted to residual DNA analysis (FastDNA™ Spin Kit and PCR). A sample of fermentation broth was collected prior to the heat treatment and its DNA content was analyzed in parallel to the process stream samples.

Only the untreated culture broth had a positive DNA signal indicated by the presence of a PCR band on an agarose gel (see arrows on FIG. 1). All other samples had a negative DNA signal indicated by the absence of a PCR band on the same agarose gel. A negative control (water) was added to evaluate the quality of the DNA analysis.

For comparison, at least two independent, standard production batches have been checked for the presence of residual DNA in their respective ultrafiltration enzyme concentrate. All samples were shown to contain substantial amounts of residual host DNA (data not shown).

Conclusion:
  The results indicate that the combination of heat treatment and subsequent flocculation of the fermentation broth had a positive effect for removing residual host DNA from the production strain of this amylase variant.

Example 2

DNA Removal from the Fermentation Broth of an Asparaginase by the Combination of Heat Treatment and Flocculation in Pilot Scale and in Production Scale A submerged fermentation of a *Bacillus subtilis* strain expressing an asparaginase was performed as known in the art.

The fermentation broth contained the protein of interest (an asparaginase) and the resulting broth had a demonstrated DNA content.

At the end of the standard fermentation the temperature of the broth was raised by means of controlled steam injection in the tank. The temperature was raised to reach 80° C. and the broth was incubated at this temperature for 80 min. Once the heat treatment was executed, the fermentation broth was transferred in another tank with mixing and cooling/heating capacity by means of jackets surrounding the tank: the broth was cooled to reach approximately 15° C. and was kept at this temperature with constant mixing before being processed furthermore.

The fermentation broth was flocculated batch-wise in pilot scale according to the following instructions:

| Component | Amount | Concentration | Supplier |
|---|---|---|---|
| Heat treated fermentation broth | 330 kg | — | |
| Tap water | 1460 kg | — | |
| CaCl$_2$ | 8.05 kg | 100% | Tetra, Helsingborg, Sweden |
| GC850 ™ | 8.15 kg | 100% | Kemira Water, Copenhagen, Denmark |
| Superfloc C591 ™ | 56.7 kg | 10% | Kemira Water, Copenhagen, Denmark |
| Superfloc A130 ™ | 17.9 kg | 0.01% | Kemira Water, Copenhagen, Denmark |

The broth was diluted with warm tap water in order to reach a temperature of 35° C. through the first part of the enzyme recovery. pH was adjusted with acetic acid and/or sodium hydroxide solutions after the addition of the poly-aluminum salt GC850™ in order to reach the desired pH 9.0 set point.

The flocculated material was then submitted to a recovery process similar to the one used for standard production but down-scaled to pilot scale. All equipment units were operated according to the respective manufacturer's instructions and/or according to protocols as known in the art. The process included:

Drum filtration on a rotary vacuum drum filter,
Polish filtration on centrifugal discharge filter,
Germ filtration on disposable EKS filter modules (Pall, Lund, Sweden),
Ultrafiltration on semi-permeable UFX10 membranes (Alfa Laval, Lund, Sweden),
Final germ filtration on disposable EKS filter modules.

Samples were taken at all streams mentioned here above and submitted to residual DNA analysis (FastDNA™ Spin Kit and PCR). A sample of fermentation broth was collected prior to the heat treatment and its DNA content was analyzed in parallel to the process stream samples.

Only the untreated culture broth had a positive DNA signal indicated by the presence of a PCR band on an agarose gel (see arrows on FIG. 2). All other samples had a negative DNA signal indicated by the absence of a PCR band on the same agarose gel. A negative control (water) was added to evaluate the quality of the DNA analysis.

As a control, a similar fermentation broth was recovered according to the technique described here above but without a preliminary heat treatment. The analytical characterization of all process streams demonstrated the presence of residual DNA at all steps with a particular increase in concentration in the ultrafiltration concentrate sample (data not shown).

Example 3

One additional fermentation broth of the asparaginase producing strain, prepared as described in Example 2, was heat treated in pilot scale by means of steam injection and was flocculated with a similar recipe as described here above and which was slightly modified in terms of chemicals dosing to obtain a satisfactory cell separation (data not shown). The recovery of the enzyme was executed in pilot scale using the identical process as described here above. All process stream samples collected throughout the execution of the recovery process were proved to be void of residual DNA at the exception of the culture broth itself and the supernatant of the heat treated fermentation broth (FIG. 3).

This test particularly emphasizes the benefit in combining both heat treatment and flocculation.

Example 4

The heat treatment of the asparaginase fermentation broth, prepared as described in example 2, by means of steam injection together with the subsequent flocculation of the heat-treated fermentation broth was executed in production scale on production relevant equipment and according to instructions as known in the art. Here too, the flocculation recipe was slightly modified in terms of chemicals dosing to obtain a satisfactory cell separation; the flocculation was carried out online and not batch-wise. Process stream samples were collected as triplicates throughout the execution of the recovery process; their analysis proved that DNA could not be detected in the most concentrated enzyme solution out of the ultrafiltration unit (data not shown).

This test demonstrated that the techniques described here above can be successfully scaled up in production scale. The continuous flocculation used in production gave no different results than the batch-wise flocculation used in pilot scale, suggesting that both techniques can be executed successfully when combined with the heat treatment of the fermentation broth.

Conclusion from Examples 2, 3 and 4

These results strongly support that the combination of heat treatment with flocculation had a positive effect for removing residual host DNA from the production strain of this asparaginase strain both in pilot scale and, most importantly, in production scale.

The invention claimed is:

1. A method for removing DNA from a fermentation broth comprising a protein of interest, a microorganism producing the protein of interest, and DNA, said method comprising:
a) at the end of a fermentation, heating the fermentation broth to a temperature of at least 70° C.,
b) subsequent to step (a), adding a poly aluminium chloride to the fermentation broth, and
c) subsequent to step (b), separating flocculated material from the fermentation broth,
wherein the protein of interest is thermostable.

2. The method according to claim 1, wherein the thermostable protein of interest is a peptide.

3. The method according to claim 2, wherein the thermostable protein of interest is an enzyme selected among: hydrolases, lyases, proteases, amylases glucoamylases, pectinases, pectate lyases, cellulases, xylanases, arabinases, arbinofuranosidases, mannanases, carrageenanases, xanthanases, endoglucanases, chitinases, asparaginases, lipases, phospholipases, cutinases, lysozymes, phytases, peroxidases, lactase, glucose isomerases, xylose isomerases, esterases and phosphodiesterases.

4. The method according to claim 3, wherein the enzyme has a thermostability measured as halflife at 70° C. and pH 7.0 of at least 30 minutes.

5. The method according to claim 3, wherein the enzyme is an amylase or an asparaginase.

6. The method according to claim 1, wherein the microorganism is a bacterium or a fungus.

7. The method according to claim 6, wherein the microorganism is a fungus selected from the group consisting of *Trichoderma* and *Aspergillus* host cells.

8. The method according to claim 6, wherein the bacterium is a gram positive bacterium or a gram negative bacterium.

9. The method according to claim 1, wherein the fermentation broth is heated to a temperature of at least 75° C.

10. The method according to claim 1, wherein the fermentation broth is heated to a temperature between 70° C. and 110° C.

11. The method according to claim 1, wherein a temperature of the heated fermentation broth is kept above 70° C. for a period of at least 10 min.

12. The method according to claim 1, wherein the poly aluminium chloride is added in an amount of 0.1-10% (w/w) in the fermentation broth.

13. The method according to claim 1, wherein one or more salts or polymers are added to the fermentation broth in addition to the poly aluminium chloride.

14. The method according to claim 13, wherein the polymer is an anionic or a cationic polymer.

15. The method according to claim 1, wherein the separation in step c) is performed by centrifugation or filtration.

16. The method according to claim 1, wherein pH of the fermentation broth is adjusted to a range of pH 2 to pH 11 after addition of the poly aluminium chloride.

17. The method according to claim 1, wherein a DNA level in the fermentation broth is reduced to below 1 µg/ml.

18. The method according to claim 2, wherein the peptide is an antimicrobial peptide, a lipopeptide or a brazzein.

19. The method according to claim 7, wherein the *Trichoderma* or *Aspergillus* host cells are selected from the group consisting of *Trichoderma harzianum, Trichoderma koningii, Trichoderma longibrachiatum, Trichoderma reesei, Trichoderma viridel, Aspergillus awamori, Aspergillus fumigatus, Aspergillus foetidus, Aspergillus japonicus, Aspergillus nidulans, Aspergillus niger* and *Aspergillus oryzae.*

20. The method according to claim 8, wherein the gram positive bacterium is selected from the group consisting of *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis.*

21. The method according to claim 8, wherein the gram negative bacterium is selected from the group consisting of *Campylobacter, Escherichia, Flavobacterium, Fusobacterium, Helicobacter, Ilyobacter, Neisseria, Pseudomonas, Salmonella,* and *Ureaplasma.*

* * * * *